United States Patent
Palmer

(10) Patent No.: US 6,638,294 B1
(45) Date of Patent: Oct. 28, 2003

(54) SELF FURLING UMBRELLA FRAME FOR CAROTID FILTER

(75) Inventor: Olin Palmer, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 109 days.

(21) Appl. No.: 09/944,953

(22) Filed: Aug. 30, 2001

(51) Int. Cl.$^7$ ............................................... A61M 29/00
(52) U.S. Cl. ....................................................... 606/200
(58) Field of Search ................................ 606/200, 113, 606/114, 127, 159

(56) References Cited

U.S. PATENT DOCUMENTS

| | | |
|---|---|---|
| 5,613,981 A | 3/1997 | Boyle et al. |
| 5,769,816 A | 6/1998 | Barbut et al. |
| 5,814,064 A | 9/1998 | Daniel et al. |
| 5,910,154 A | 6/1999 | Tsugita et al. |
| 5,941,869 A | 8/1999 | Patterson et al. |
| 5,941,896 A | 8/1999 | Kerr |
| 6,152,946 A | 11/2000 | Broome et al. |
| 6,171,328 B1 | 1/2001 | Addis |
| 6,214,040 B1 | 4/2001 | Jayaraman |
| 6,346,116 B1 * | 2/2002 | Brooks et al. ............ 606/200 |
| 6,391,044 B1 * | 5/2002 | Yadav et al. ............. 606/200 |

* cited by examiner

Primary Examiner—Kevin T. Truong
(74) Attorney, Agent, or Firm—Fulwider Patton Lee & Utecht, LLP

(57) ABSTRACT

A capture device for removal of clots and foreign bodies from vasculature or filtering of particulate from blood flow. The parachute-like capture device is connected to an elongate wire located within a longitudinally elongated tubular member. The capture device is radially expandable and is refolded to a reduced profile during contraction.

24 Claims, 3 Drawing Sheets

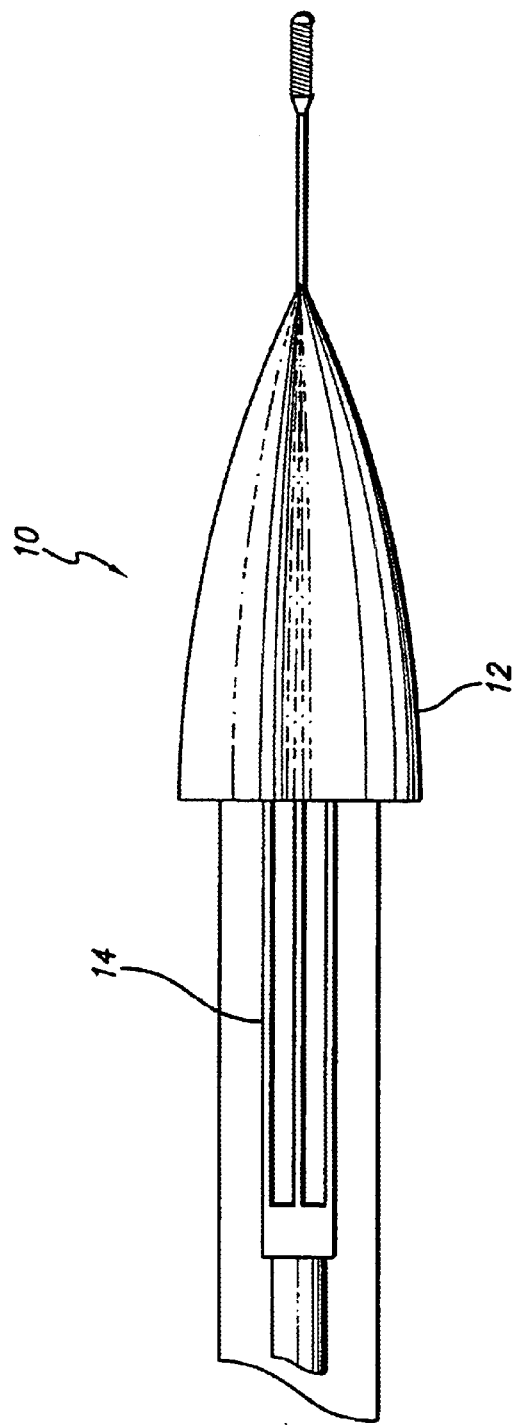
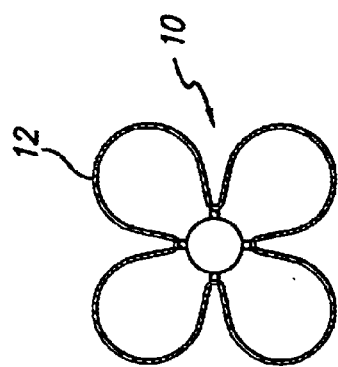

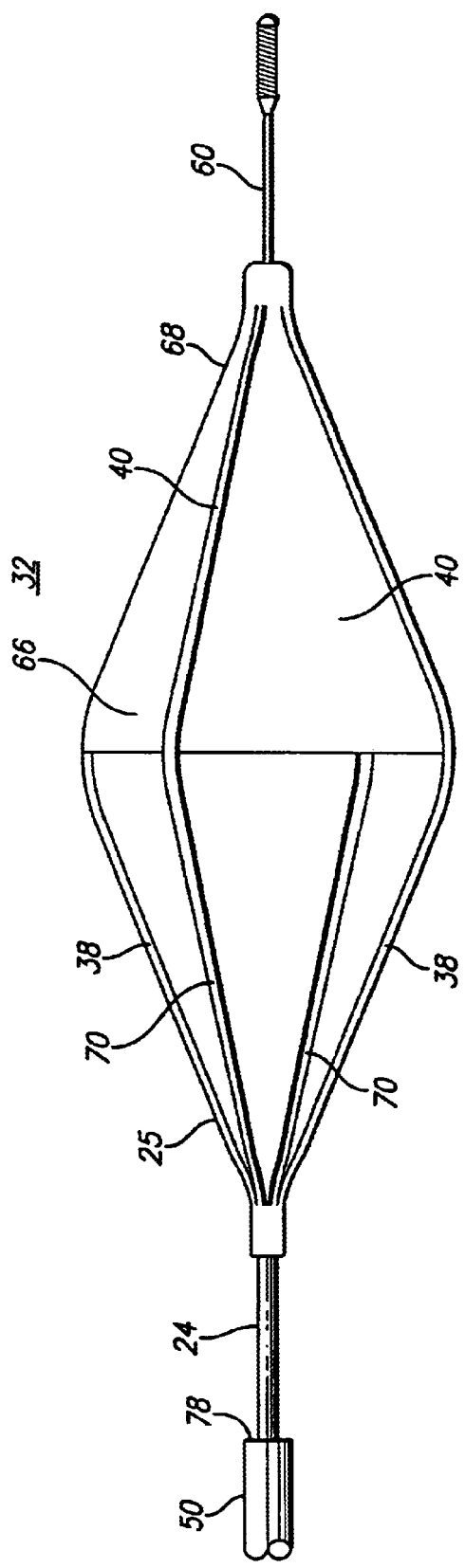
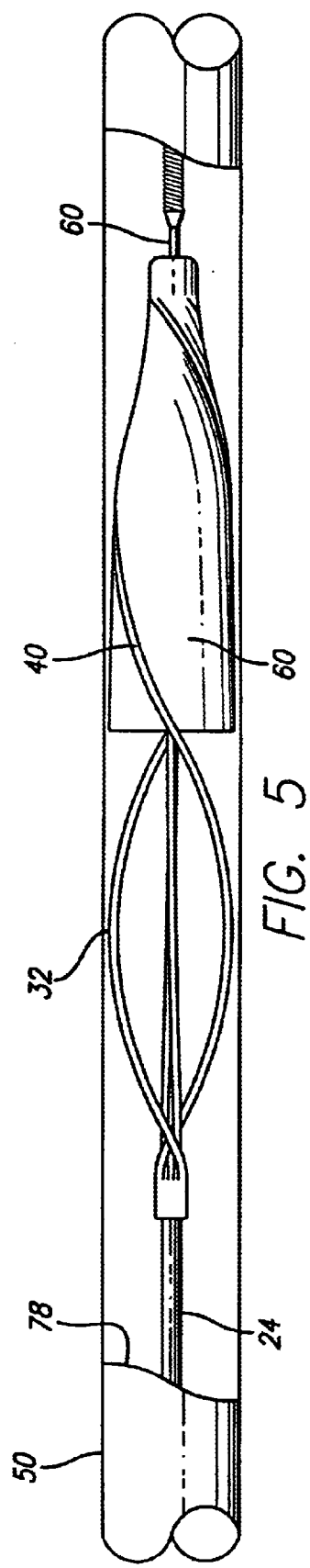

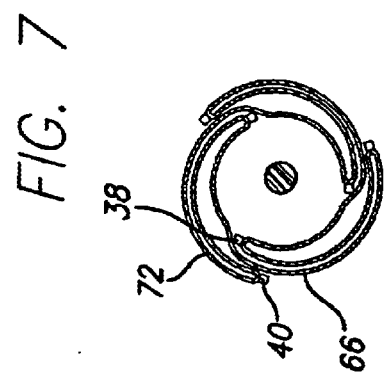
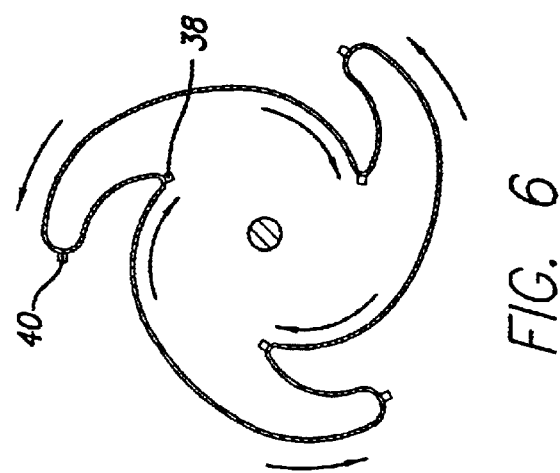
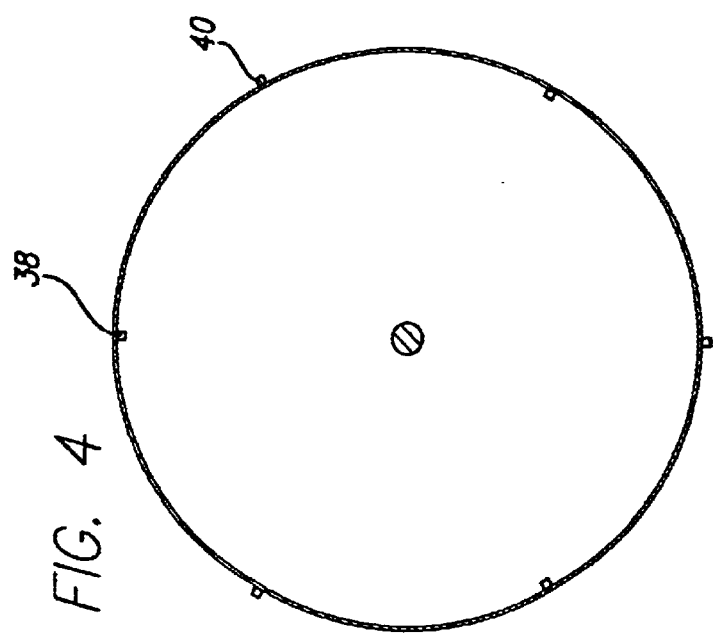

SELF FURLING UMBRELLA FRAME FOR CAROTID FILTER

BACKGROUND OF THE INVENTION

This invention relates generally to medical devices used during vascular intervention, and more particularly, concerns medical devices that are useful in treating thromboembolic disorders and for removal of foreign bodies in the vascular system.

Thromboembolic disorders, such as stroke, pulmonary embolism, peripheral thrombosis, atherosclerosis, and the like, affect many people. These disorders are a major cause of morbidity and mortality in the United States and throughout the world. Thromboembolic events are characterized by an occlusion of a blood vessel. The occlusion can be caused by a clot which is viscoelastic (jelly-like) and is comprised of platelets, fibrinogen, and other clotting proteins.

When an artery is occluded by a clot, tissue ischemia (lack of oxygen and nutrients) develops. The ischemia will progress to tissue infarction (cell death) if the occlusion persists. Infarction does not develop or is greatly limited if the flow of blood is reestablished rapidly. Failure to reestablish blood-flow can lead to the loss of limb, angina pectoris, myocardial infarction, stroke, or even death.

Occlusion of the venous circulation by thrombi leads to blood stasis which can cause numerous problems. The majority of pulmonary embolisms are caused by emboli that originate in the peripheral venous system. Reestablishing blood flow and removal of the thrombus is highly desirable.

There are many existing techniques employed to reestablish blood flow in an occluded vessel. One common surgical technique, an embolectomy, involves incising a blood vessel and introducing a balloon-tipped device (such as a Fogarty catheter) to the location of the occlusion. The balloon is then inflated at a point beyond the clot and used to translate the obstructing material back to the point of incision. The obstructing material is then removed by the surgeon. While such surgical techniques have been useful, exposing a patient to surgery may be traumatic and is best avoided when possible. Additionally, the use of a Fogarty catheter may be problematic due to the possible risk of damaging the interior lining of the vessel as the catheter is being withdrawn.

Percutaneous methods are also utilized for reestablishing blood flow.

A common percutaneous technique is referred to as balloon angioplasty where a balloon-tipped catheter is introduced into a blood vessel, typically through an introducing catheter. The balloon-tipped catheter is then advanced to the point of the occlusion and inflated in order to dilate the stenosis. Balloon angioplasty is appropriate for treating vessel stenosis but is generally not effective for treating acute thromboembolisms.

Another percutaneous technique is to place a microcatheter near the clot and infuse Streptokinase, Urokinase, or other thrombolytic agents to dissolve the clot. Unfortunately, thrombolysis typically takes hours to days to be successful. Additionally, thrombolytic agents can cause hemorrhage and in many patients the agents cannot be used at all.

Another problematic area is the removal of foreign bodies. Foreign bodies introduced into the circulation can be fragments of catheters, pace-maker electrodes, guide wires, and erroneously placed embolic material such as thrombogenic coils. There exists retrieval devices for the removal of foreign bodies, certain of such devices form a loop that can ensnare the foreign material by decreasing the size of the diameter of the loop around the foreign body. The use of such removal devices can be difficult and sometimes unsuccessful.

Moreover, systems heretofore disclosed in the art are generally limited by size compatibility and the increase in vessel size as the emboli is drawn out from the distal vascular occlusion location to a more proximal location near the heart. If the embolectomy device is too large for the vessel it will not deploy correctly to capture the clot or foreign body, and if too small in diameter it cannot capture clots or foreign bodies across the entire cross section of the blood vessel. Additionally, if the embolectomy device is too small in retaining volume then as the device is retracted the excess material being removed can spill out and be carried by flow back to occlude another distal vessel.

Various thrombectomy and foreign matter removal devices have been disclosed in the art. However, such devices have been found to have structures which are either highly complex or lacking in sufficient retaining structure. Disadvantages associated with the devices having highly complex structure include difficulty in manufacturability as well as difficulty in use in conjunction with microcatheters. Recent developments in the removal device art features umbrella filter devices having self folding capabilities. Typically, these filters fold into a pleated condition, wherein the pleats extend radially and can obstruct retraction of the device into the microcatheter sheathing.

What has been needed and heretofore unavailable is an extraction device that can be easily and controllably deployed into and retracted from the circulatory system for the effective removal of clots and foreign bodies. There is also a need for a system that can be used as a temporary arterial or venous filter to capture and remove thromboemboli generated during endovascular procedures. Moreover, due to difficult-to-access anatomy such as the cerebral vasculature and the neurovasculature, the invention should possess a small collapsed profile and preferably be expandable to allow the device to be delivered through the lumen of commercially available catheters. The present invention satisfies these needs.

SUMMARY OF THE INVENTION

Briefly, and in general terms, the present invention is directed to an improvement in devices for removing embolic or foreign material from a vessel. In one aspect, the present invention is a medical device which includes an elongate member having a proximal end portion for manipulation by an operator and a distal end portion which is attached to a filter or capture device. This filter or capture device includes a body having a plurality of struts extending from the elongate member to a basket or cage structure. The basket or cage structure includes a proximally directed opening and a generally conical shape in an expanded configuration. When the basket or cage is placed in a compressed or closed configuration pleats are formed in the basket or cage and certain of the struts operate to fold the pleats to thereby define a relatively sleek profile.

In another aspect of the invention, the struts include a first set of arms and a second set of arms, single members of which are interspaced between adjacent pairs of arms of the first set when the medical device is in an expanded configuration. Each of the arms of the second set include a proximal portion defining a slight helix so that when the medical device is compressed radially, the arms of the second set rotate with respect to the arms of the first set. Such action accomplishes the folding or furling of the pleats of the basket or cage. It is contemplated that the medical device of the present invention can further include an atramatic distal end portion projecting distally from the cage or basket. Additionally, the cage or basket is defined by various structures including weaved fabrics or interconnected metal struts with or without a membrane extending thereacross.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 (prior art) is a partial cross-sectional view depicting an extraction device depicting a collapsed filter device.

FIG. 2 is a end view of the extraction device depicted in FIG. 1.

FIG. 3 is a side partial cutaway view of a parachute-like extraction device in an expanded condition.

FIG. 4 is a cross-sectional view of the expanded extraction device depicted in FIG. 3.

FIG. 5 is a side, cutaway view of the parachute-like extraction device in a collapsed self folded condition within a catheter.

FIG. 6 is a cross-sectional view of a first stage in collapsing the parachute-like extraction device shown in FIG. 4, depicting the helix rotation of the outer structural members relative to the inner structural members.

FIG. 7 is a cross-sectional view of a second stage in collapsing the parachute-like extraction device shown in FIG. 4.

DETAILED DESCRIPTION OF THE PREFERRED EMBODIMENTS

The present invention is useful for the removal of embolic or foreign material from vasculature. The present invention is intended to be used in various sized vessels and in vessels having varying degrees of tortuosity. Of particular significance is the contemplated use of the preferred embodiment in the highly tortuous cerebral vasculature or neurovasculature. Moreover, the disclosed capture device is characterized by having an expanded structure that is useful as a filter device, and a contracted structure having a low profile folded condition to facilitate an atraumatic delivery and retraction of the system.

Referring to FIGS. 1–2, a collapsed and folded capture device 10 existing in the art is depicted having pleats 12 which extend radially when the capture device 10 is in a folded position. As seen in FIG. 1, the radially extended, folded pleats may be problematic when the capture device is retracted within a catheter sheath 14. That is, the pleats may get in the way when retracting the capture device 10 within the sheath 14. This obstruction may result in the re-release of any captured embolic or foreign material back into the vasculature. The present invention solves this problem by improving the folding technique and reducing the cross-sectional profile of the collapsed capture device.

Referring to FIG. 3, there is shown an embodiment of the present invention, in an expanded condition, which is adapted to capture embolic or foreign material found within a vessel. In a presently preferred first embodiment, a parachute-like capture device 32 includes an elongate wire 24 having a basket or cage 25 attached to a distal end thereof. The cage includes a plurality of struts or structural members 38, 40 extending longitudinally from the elongate wire 24. The elongate wire 24 is configured longitudinally within a delivery catheter 50. The elongate wire 24 can additionally define a tubular structure having an internal lumen. The distal end 60 of the capture device 32 can be defined by an atraumatic tip extending longitudinally and having a generally helical substructure. Alternatively, the tip can be omitted so that the device can be routed over a guidewire.

The capture device 32 includes a frame having a plurality of structural members 38, 40. The plurality of structural members 38, 40 embody a plurality of inner structural members 38 and a plurality of outer structural members 40 each being configured to expand the capture device 32 into a parachute-like structure 32, and to collapse the capture device 32 into a contracted condition (See FIG. 5). Configured between or across the struts may be mesh, knitted, or perforated material 66 to thereby define a parachute-like capture assembly. The mesh or knitted portion 66 is connected to the struts 38, 40 by conventional means, such as by sewing or gluing. The knitted or mesh portion 66 may form a cone-like configuration with its most distal end 68 defining the apex of the cone. It is to be recognized, however, that other basket configurations may also be employed. The parachute-like capture device 32 is characterized by providing structure which may be particularly useful in collecting matter in its hollow interior.

The mesh or knitted portion 66 can include micropores which permit blood flow or can be replaced with other materials such as impermeable or permeable elastomers. Additionally, the entire basket portion can be made of the same material which is laser cut to a desired configuration. The thinner walled material could be used to span the area between struts.

In a preferred embodiment of the present invention, the capture device 32 expands radially with respect to the elongate wire 24 into a generally parachute-like member having a proximal end and a distal end. As the elongate wire is distally advanced with respect to the catheter 50, the plurality of inner struts 38 and outer struts 40 expand to project the capture device 32 into a parachute-like frame.

As shown in FIGS. 4–7, in an expanded condition, the inner struts 38 and the outer struts 40 are configured in an alternative pattern where one inner strut 38 is interspersed between two outer struts 40. As the capture device 32 is collapsed by retracting the elongate wire 24 proximally within a catheter 50, the outer struts 40 having a slight helix configuration at a proximal region 70, rotate relative to the inner struts 38. The rotation of the outer struts 38 operates to fold the capture device 32, wherein the pleats 72 of the parachute are furled into a contracted condition. The relatively reduced cross-section of the folded capture device 32 allows the capture device to be more easily retracted into the delivery catheter 50 sheath without intrusion from the pleated folds 72.

It is to be recognized that all struts can include a slight helix configuration so that all struts shift radial position when the device is collapsed. In such a design, certain struts (e.g., outer struts) can be configured to shift a greater amount than other struts so that the desired furling of the pleats is accomplished.

The elongate wire 24 may include a conventional guidewire or other wire structure having similar properties. One material of choice may be Nitinol. The elongate wire outer diameter is such that it can easily slide within a lumen 78 of the catheter 50. Generally, the elongate wire 24 has a length greater than that of the catheter 50 so that its proximal end can be grasped by an operator and so that the elongate wire 24 can be advanced and withdrawn independently of the catheter 50.

The delivery catheter 50 can be any commercially available catheter that is made from any appropriate biologically compatible material. Typically, the catheter will have a single lumen 28 as constructed out of a flexible polymer material such as silicone, rubber, polyvinylchloride, polyeurothanes, polyesters, polytetrafluoroethylene and the like. The catheter has to be flexible enough and long enough to navigate through blood vessels to the occluded vessel where clots or other foreign bodies are located. Typically, the catheter will range in length from about 20 to about 175 centimeters. The outer diameter of the catheter can also vary. That is, the outer diameter will range from about 2 to about 10 F (1 F equals 0.013 inch). The inner diameter will range from about 1 to about 9 F.

The struts 38, 40 can also be made from any biologically compatible material, such as Nitinol. Although the device is intended to be self-expanding, structure can be provided to accomplish expansion in a device that is not self-expanding. In an embodiment where the elongate wire 24 defines a tubular structure, for example, an elongate member can be configured through the elongate wire (tube) 24 and placed into engagement with the distal end 68 of the capture device 32. Relative movement between the elongate member and elongate wire (tube) can accomplish the opening and closing of the capture device 50.

In use, the capture device 32 and catheter 50 are inserted into a patient's vasculature using conventional techniques, fluoroscopy or other conventional means. The elongate capture device 32 and catheter 50 are then advanced within a patient's vasculature to a location near the clot or foreign body to be extracted. Through relative movement between the catheter 50 and capture device 32, the capture device 32 is deployed beyond the catheter 50 and allowed to assume an expanded configuration. The capture device 32 is then placed or manipulated to gather the unwanted material and is retracted back within the catheter 50. Retraction of the device back within the catheter 50 is made easy due to the folding action accomplished by the interaction between the second set of struts 40 and the catheter 50. That is, when retracted, the second set of struts 40 engage a lumen defined by the catheter 40 to thereby compress the device into a small profile.

It is also contemplated that the present invention can be used as a filter in a blood vessel. In such a situation, the above-described capture device is deployed within a blood vessel and held stationary for a period of time sufficient for the extractor to filter unwanted material from a patient's bloodstream.

Thus, a capture system is disclosed which allows for the removal of thromboembolic material and foreign bodies from a blood vessel. While several particular forms and applications of the invention have been illustrated and described, it will be apparent to those skilled in the art that many more modifications are possible without departing from the spirit and scope of the invention. The invention, therefore, is not to be restricted except in the spirit of claims appended hereto.

What is claimed:

1. A system for capturing embolic or foreign material in a vessel, comprising:
   an elongate tubular member having a proximal end and a distal end;
   an elongate wire having a proximal end and a distal end, the elongate wire being positionable within the elongate tubular member;
   a capturing structure operatively connected to the elongate wire, having an expanded condition and a contracted position, the capturing structure further having an inner surface and an outer surface forming a parachute-like structure in the expanded condition; and
   a plurality of inner struts attached to the capturing structure inner surface and a plurality of outer struts attached to the capturing structure outer surface, the capture device assuming a self folding position in the contracted condition as the outer struts rotate with respect to the inner struts.

2. The system of claim 1, wherein the capture device expands radially with respect to the elongate wire into a generally parachute-like member having a proximal end and a distal end, the proximal end further comprising an orifice or plurality of orifices through which blood can flow.

3. The system of claim 1, wherein the inner and outer struts are configured in an alternating pattern when in an expanded configuration.

4. The system of claim 1, wherein the struts are biased radially outward.

5. The system of claim 1, wherein the inner struts are attached to the elongate wire.

6. The system of claim 1, wherein the outer struts are attached to the elongate wire.

7. The system of claim 1, the inner struts and the outer struts further comprising nitinol.

8. The system of claim 1, the capture device further comprises an orifice, wherein the orifice can be made to contract by retracting the distal end of the elongate wire member with respect to the elongate tubular member.

9. The system of claim 1, the inner or outer struts further comprising a slight helix at a proximal end thereof.

10. The system of claim 1, the capturing structure further comprising a semi-permeable membrane.

11. The system of claim 1, the capturing structure comprising a mesh structure.

12. The system of claim 1, the capturing structure further comprising at least one pore that is sized to allow the substantially unimpeded flow of blood therethrough.

13. The system of claim 1, wherein the elongate tubular member is a microcatheter.

14. The system of claim 1, the capturing structure further comprising a knitted structure.

15. The system of claim 1, wherein the inner struts are laterally attached to the capturing structure inner surface.

16. The system of claim 1, wherein the outer struts are laterally attached to the capturing structure outer surface.

17. A system for capturing embolic or foreign material in a vessel, comprising:
   an elongate tubular member having a proximal end and a distal end;
   an elongate wire having a proximal end and a distal end, the elongate wire being positionable within the elongate tubular member;
   a capturing structure operatively connected to the elongate wire having an expanded condition and a contracted position, the capturing structure forming a parachute-like structure in the expanded condition;
   a plurality of first struts having proximal ends and distal ends, the distal ends being attached to the capturing structure and the proximal ends being attached to the elongated wire; and a plurality of second struts having proximal ends and distal ends, the distal ends being attached to the capturing structure and the proximal ends being attached to the elongated wire, the proximal ends including a partial helix configuration.

18. The system of claim 17, wherein the capturing structure assumes a folded position in the contracted condition.

19. The system of claim 17, wherein the capture device expands radially with respect to the elongate wire into a generally parachute-like member having a proximal end and a distal end, wherein the proximal end is defined by an orifice through which blood can flow.

20. The system of claim 17, wherein the plurality of first struts and second struts are biased radially outward.

21. The system of claim 17, the capture device further comprising an orifice, wherein the orifice can be made to close by retracting the distal end of the elongate wire member proximally, refolding the capture device and reducing the profile for an atraumatic retraction of the device.

22. The system of claim 17, the capturing structure comprising a mesh structure.

23. The system of claim 17, the capturing structure comprising a membrane.

24. The system of claim 17, wherein the capturing structure has at least one pore that is sized to allow the substantially unimpeded flow of blood therethrough.

\* \* \* \* \*

UNITED STATES PATENT AND TRADEMARK OFFICE
CERTIFICATE OF CORRECTION

PATENT NO.     : 6,638,294 B1
DATED          : October 28, 2003
INVENTOR(S)    : Olin Palmer It is certified that error appears in the above-identified patent and that said Letters Patent is hereby corrected as shown below:

<u>Column 6,</u>
Line 62, after "structure", add -- further having an inner surface and an outer surface --.
Line 66, after "structure", add -- inner surface --.

<u>Column 7,</u>
Line 3, after "structure", add -- outer surface --.

Signed and Sealed this

Second Day of March, 2004

JON W. DUDAS
*Acting Director of the United States Patent and Trademark Office*